(12) United States Patent
Lee et al.

(10) Patent No.: US 9,783,779 B2
(45) Date of Patent: Oct. 10, 2017

(54) ARTIFICIAL OOCYTE ACTIVATION

(71) Applicants: Kiho Lee, Columbia, MO (US); Randall S. Prather, Columbia, MO (US)

(72) Inventors: Kiho Lee, Columbia, MO (US); Randall S. Prather, Columbia, MO (US)

(73) Assignee: The Curators of the University of Missouri, Colombia, MO (US)

( * ) Notice: Subject to any disclaimer, the term of this patent is extended or adjusted under 35 U.S.C. 154(b) by 22 days.

(21) Appl. No.: 14/554,504

(22) Filed: Nov. 26, 2014

(65) Prior Publication Data

US 2015/0150153 A1    May 28, 2015

Related U.S. Application Data

(60) Provisional application No. 61/997,176, filed on May 23, 2014, provisional application No. 61/963,246, filed on Nov. 27, 2013.

(51) Int. Cl.

| | |
|---|---|
| C12N 5/00 | (2006.01) |
| C12N 5/02 | (2006.01) |
| C12N 15/00 | (2006.01) |
| C12N 5/075 | (2010.01) |
| A01K 67/027 | (2006.01) |
| C12N 15/877 | (2010.01) |

(52) U.S. Cl.
CPC ........ *C12N 5/0609* (2013.01); *A01K 67/0273* (2013.01); *C12N 15/877* (2013.01); *C12N 15/8778* (2013.01); *A01K 2227/108* (2013.01); *C12N 2500/14* (2013.01); *C12N 2500/22* (2013.01); *C12N 2501/405* (2013.01); *C12N 2517/04* (2013.01); *C12N 2517/10* (2013.01)

(58) Field of Classification Search
CPC .............. C12N 5/0609; C12N 15/8778; A01K 67/0273
See application file for complete search history.

(56) References Cited

U.S. PATENT DOCUMENTS

| | | |
|---|---|---|
| 4,994,384 A | 2/1991 | Prather et al. |
| 5,496,720 A | 3/1996 | Susko-Parrish et al. |
| 6,077,710 A | 6/2000 | Susko-Parrish et al. |
| 6,211,429 B1 | 4/2001 | Machaty et al. |
| 7,323,620 B2 | 1/2008 | Woods et al. |
| 7,531,715 B1 | 5/2009 | Campbell |
| 8,647,872 B2 | 2/2014 | Roh et al. |
| 8,772,029 B2 | 7/2014 | Woodruff et al. |
| 2003/0066100 A1 | 4/2003 | Machaty et al. |

OTHER PUBLICATIONS

US 7,531,815, 05/2009, Ward et al. (withdrawn)
Hyun, 2001, Retinal Cell biology, 42:460-465.*
Radford, 2013, Current Opin Chem Biol, 17:129-136.*
Lee et al., "Pig oocyte activation using a $Zn^{2+}$ chelator, TPEN," *Theriogenology* 84:1024-1032, 2015.
Bernhardt et al., "A zinc-dependent mechanism regulates meiotic progression in mammalian oocytes," *Biol Reprod* 86(4):114, 2012.
Bing et al., "Parthenogenetic activation and subsequent development of porcine oocytes activated by a combined electric pulse and butyrolactone I treatment," *J Reprod Dev* 49:159-166, 2003.
Bos-Mikich et al., "Meiotic and mitotic Ca2+ oscillations affect cell composition in resulting blastocysts," *Dev Biol* 182:172-179, 1997.
Burggren, "Epigenetics as a source of variation in comparative animal physiology—or—Lamarck is lookin' pretty good these days," *J Experimental Biology* 217:682-889, 2014.
Donadelli et al., "Zinc depletion efficiently inhibits pancreatic cancer cell growth by increasing the ratio of antiproliferative-proliferative genes," *J Cell Biochem* 104:202-212, 2008.
Ducibella et al., "Egg-to-embryo transition is driven by differential responses to Ca(2+) oscillation number," *Dev Biol* 250:280-291, 2002.
Ducibella et al., "The roles of Ca2+, downstream protein kinases, and oscillatory signaling in regulating fertilization and the activation of development," (author manuscripts); published in the final form of *Dev Biol* 315: 257-279, 2008.
Ducibella, "The cortical reaction and development of activation competence in mammalian oocytes," *Hum Reprod Update* 2:29-42, 1996.
First et al., "Genomic potential in mammals," *Differentiation* 48(1):1-8, 1991.
Hansen et al., "CaMKII and polo-like kinase 1 sequentially phosphorylate the cytostatic factor Emi2-XErp1 to trigger its destruction and meiotic exit," *PNAS USA* 103:608-613, 2006.
International Search Report and Written Opinion for PCT/US2014/067588, dated Mar. 2, 2015.
Jones, "Intracellular calcium in the fertilization and development of mammalian eggs," *Clin Exp Pharmacol Physiol* 34:1084-1089, 2007.
Kikuchi et al., "Maturation-M-phase promoting factor: a regulator of aging in porcine oocytes," *Biol Reprod* 63:715-722, 2000.
Kim et al., "Zinc availability regulates exit from meiosis in maturing mammalian oocytes," *Nat Chem Biol* 6:674-681, 2010.
Kim et al., "Zinc sparks are triggered by fertilization and facilitate cell cycle resumption in mammalian eggs," (author manuscripts); published in the final form of *ACS Chem Biol* 6:716-723, 2011.
Kline et al., "Repetitive calcium transients and the role of calcium in exocytosis and cell cycle activation in the mouse egg," *Dev Biol* 149:80-89, 1992.

(Continued)

*Primary Examiner* — Valarie Bertoglio
(74) *Attorney, Agent, or Firm* — Dentons US LLP

(57) ABSTRACT

The present invention provides novel methods for improving the efficiency of artificial activation of unfertilized mammalian oocytes by reducing the intracellular concentration of $Zn^{2+}$ in the oocyte. The methods of the invention may additionally comprise a preceding step of increasing the intracellular concentration of $Ca^{2+}$ in the oocyte prior to reduction of the intracellular $Zn^{2+}$ concentration. The invention further provides unfertilized oocytes activated by the disclosed methods and viable mammalian animals produced from unfertilized oocytes activated by the disclosed methods.

4 Claims, 2 Drawing Sheets

(56) References Cited

OTHER PUBLICATIONS

Kong et al., "Zinc maintains prophase I arrest in mouse oocytes through regulation of the MOS-MAPK pathway," *Biology of Reproduction* 87(1)11:12-3, 2012.
Kwon et al., "Production of biallelic CMP-Neu5Ac hydroxylase knock-out pigs," *Sci Rep* 3:1981, 2013.
Lai et al., "Production of alpha-1, 3-galactosyltransferase knockout pigs by nuclear transfer cloning," *Science, American Association for the Advancement of Science*, US 295:1089-1092, 2002, abstract.
Lai et al., "Production of cloned pigs by using somatic cells as donors," *Cloning Stem Cells* 5:233-241, 2003.
Lawrence et al., "The effects of a Ca2+ chelator and heavy-metal-ion chelators upon Ca2+ oscillations and activation at fertilization in mouse eggs suggest a role for repetitive Ca2+ increases," *Biochem J* 335( Pt 2):335-342, 1998.
Lee et al., "A novel method to increase the developmental potential of activated oocytes by using the Zn2+ chelator tpen [N,N,N',N'-tetrakis (2-Pyridylmethyl) ethylenediamine]," International Embryo Transfer Society Meeting presentation, 2014.
Lee et al., "A novel method to increase the developmental potential of activated oocytes by using the Zn2+ chelator tpen (N,N,N',N'-tetrakis (2-Pyridylmethyl) ethylenediamine)," *Reproduction, Fertility and Development* 26(1)189, 2014.
Lee et al., "Engraftment of human iPS cells and allogeneic porcine cells into pigs with inactivated RAG2 and accompanying severe combined immunodeficiency," *PNAS USA* 111:7260-7265, 2014.
Lee et al., "Piglets produced from cloned blastocysts cultured in vitro with GM-CSF," (author manuscripts); published in the final form of *Mol Reprod Dev* 80:145-154, 2013.
Liu et al., "Calcium elevation at fertilization coordinates phosphorylation of XErp1-Emi2 by Plx1 and CaMK II to release metaphase arrest by cytostatic factor," *Curr Biol* 15:1458-1468, 2005.
Machaty et al., "Na+Ca2+ exchanger in porcine oocytes," *Biology of Reproduction* 67:1133-1139, 2002.
Machaty et al., "Complete activation of porcine oocytes induced by the sulfhydryl reagent, thimerosal," *Biol Reprod* 57:1123-1127, 1997.
Madgwick et al., "Mouse Emi2 is required to enter meiosis II by reestablishing cyclin B1 during interkinesis," *J Cell Biol* 174:791-801, 2006.
Markoulaki et al. "Fertilization stimulates long-lasting oscillations of CaMKII activity in mouse eggs," *Dev Biol* 272:15-25, 2004.
McCarrey, "Distinctions between transgenerational and non-transgenerational epimutations," *Molecular and Cellular Endocrinology*, 2014.
Mendivil-Perez et al., "TPEN Induces apoptosis independently of zinc chelator activity in a model of acute lymphoblastic leukemia and ex vivo acute leukemia cells through oxidative stress and mitochondria caspase-3- and AIF-dependent pathways," *Oxid Med Cell Longev* 2012: 313275, 2012.
Nanassy et al., "Changes in MPF and MAPK activities in porcine oocytes activated by different methods," *Theriogenology* 68:146-152, 2007.
Nanassy et al., "Effects of activation methods and culture conditions on development of parthenogenetic porcine embryos," *Anim Reprod Sci* 104:264-274, 2008.
Rauh et al., "Calcium triggers exit from meiosis II by targeting the APC-C inhibitor XErp1 for degradation," *Nature* 437:1048-1052, 2005.
Saunders et al. "PLC zeta: a sperm-specific trigger of Ca(2+) oscillations in eggs and embryo development," *Development* 129: 3533-3544, 2002.
Sun et al., "A comparison of intracellular changes in porcine eggs after fertilization and electroactivation," *Development* 115:947-956, 1992.
Sun et al., "Zinc regulates the ability of Cdc25C to activate MPF-cdk1," *J Cell Physiol* 213:98-104, 2007.
Suzuki et al., "Full-term mouse development by abolishing Zn2+-dependent metaphase II arrest without Ca2+ release," *Development* 137:2659-2669, 2010.
Swann, "Dynamics of the calcium signal that triggers mammalian egg activation," *Int Rev Cytol* 152:183-222, 1994.
Vitullo et al., "Repetitive calcium stimuli drive meiotic resumption and pronuclear development during mouse oocyte activation," *Dev Biol* 151:128-136, 1992.
Whitworth et al., "Use of the CRISPR-Cas9 System to produce genetically engineered pigs from in vitro-derived oocytes and embryos," *Biology of Reproduction* 91(3):78, 1-13, 2014.
Whyte et al., "Gene targeting with zinc finger nucleases to produce cloned eGFP knockout pigs," *Mol Reprod Dev* 78:2, 2011.
Yoshioka et al., "Birth of piglets derived from porcine zygotes cultured in a chemically defined medium," *Biol Reprod* 66:112-119, 2002.
Zhao et al., "Significant improvement in cloning efficiency of an inbred miniature pig by histone deacetylase inhibitor treatment after somatic cell nuclear transfer," *Biol Reprod* 81:525-530, 2009.
Zhao et al., "Zinc depletion activates porcine metaphase II oocytes independently of the protein kinase C pathway," *In Vitro Cell Dev Biol Anim*, 2014.
Zhao et al., "Zinc regulates meiotic resumption in porcine oocytes via a protein kinase C-related pathway," *PLoS One* 9:e102097, 2014.

\* cited by examiner

ARTIFICIAL OOCYTE ACTIVATION

CROSS REFERENCE TO RELATED APPLICATIONS

This application claims the benefit of U.S. Provisional Application Nos. 61/963,246, filed Nov. 27, 2013, and 61/997,176, filed May 23, 2014, herein incorporated by reference in their entirety.

STATEMENT REGARDING FEDERALLY SPONSORED RESEARCH

This invention was made with government support under grant numbers U42 RR018877 and U42 OD011140 awarded by the National Institutes of Health. The government has certain rights in the invention.

FIELD OF THE INVENTION

The present invention relates to the fields of animal husbandry and biomedicine, more specifically, to a method for improving the cloning of mammals.

BACKGROUND OF THE INVENTION

Somatic cell nuclear transfer (SCNT), i.e., cloning, can be used to generate genetically engineered animals, preserve endangered species, and produce animals with a select genetic background. However, current SCNT technology is inefficient as only one percent of generated embryos are able to reach term development. One of the factors that contributes to the poor efficiency is the effectiveness of the artificial oocyte activation process, an essential procedure in SCNT. There is a great need for better approaches for artificial oocyte activation.

SUMMARY OF THE INVENTION

In one aspect, the present invention provides a method of activating an unfertilized livestock or domestic mammalian oocyte comprising decreasing intracellular $Zn^{2+}$ concentration of the oocyte by contacting the oocyte with a $Zn^{2+}$ binding moiety. In one embodiment, the $Zn^{2+}$ binding moiety comprises a concentration of between approximately 10 µM to approximately 500 µM, for instance, between approximately 100 µM to approximately 250 µM, such as approximately 200 µM. In another embodiment, the $Zn^{2+}$ binding moiety contacts the oocyte for a period of time comprising between approximately 1 minute to approximately 5 hours, for instance, between approximately 30 minutes to approximately 2.5 hours, such as approximately 30 minutes.

In further embodiments, the present method of activating an unfertilized livestock or domestic mammalian oocyte additionally comprises the step of increasing intracellular $Ca^{2+}$ concentration of the oocyte prior to decreasing the intracellular $Zn^{2+}$ concentration of the oocyte. In one embodiment, the intracellular $Ca^{2+}$ concentration of the oocyte is not increased in an amount sufficient to induce oocyte activation, for instance, the intracellular $Ca^{2+}$ concentration of the oocyte may be increased approximately ten times less than the amount sufficient to induce oocyte activation. In certain embodiments, in methods where the intracellular $Ca^{2+}$ concentration of the oocyte is not increased in an amount sufficient to induce oocyte activation, the $Zn^{2+}$ binding moiety may comprise a concentration of between approximately 1 µM to approximately 500 µM, for instance between approximately 100 µM to approximately 200 µM, such as approximately 200 µM. In other embodiments, in methods where the intracellular $Ca^{2+}$ concentration of the oocyte is not increased in an amount sufficient to induce oocyte activation, the $Zn^{2+}$ binding moiety may contact the oocyte for a period of time comprising between approximately 1 minutes to approximately 12 hours, for instance, between approximately 10 minutes to approximately 2 hours, such as approximately 30 minutes.

In still further embodiments, the intracellular $Ca^{2+}$ concentration of the oocyte may be increased in an amount sufficient to induce oocyte activation. In certain embodiments, in methods where the intracellular $Ca^{2+}$ concentration of the oocyte is increased in an amount sufficient to induce oocyte activation, the $Zn^{2+}$ binding moiety may comprise a concentration of between approximately 0.1 µM to approximately 100 µM, for instance, between approximately 1 µM to approximately 10 µM, such as approximately 5 µM or approximately 10 µM. In other embodiments, in methods where the intracellular $Ca^{2+}$ concentration of the oocyte is increased in an amount sufficient to induce oocyte activation, the $Zn^{2+}$ binding moiety contacts the oocyte for a period of time comprising between approximately 1 minutes to approximately 5 hours, for instance, between approximately 10 minutes to approximately 30 minutes, such as approximately 30 minutes.

In certain embodiments, in methods of the present invention the intracellular $Ca^{2+}$ concentration of the oocyte is increased by chemical or physical means or a combination thereof that induce calcium entry into the oocyte or release of internal calcium stores. In particular embodiments, the increase in the intracellular $Ca^{2+}$ concentration of the oocyte by chemical means comprises treatment with a calcium containing medium, a calcium salt containing medium, thimerosal containing medium, ethanol containing medium, inositol trisphosphate containing medium, a calcium ionophore containing medium, a sodium-free medium or a combination thereof. For instance, In some embodiments, the chemical treatment comprises treatment with a medium comprising a $Ca^{2+}$ concentration of between approximately 0.1 mM and approximately 250 mM, for instance, between approximately 0.1 mM and 1 mM. In other embodiments, in methods of the present invention, the increase in the intracellular $Ca^{2+}$ concentration of the oocyte by physical means comprises application of an electrical stimulus.

In yet a further embodiment of the present invention, the $Zn^{2+}$ binding moiety comprises TPEN (N,N,N',N'-tetrakis (2-pyridylmethyl)ethane-1,2-diamine). In other embodiments, the unfertilized livestock or domestic mammalian oocyte is a nuclear transfer oocyte. In additional embodiments, the unfertilized livestock or domestic mammalian oocyte is selected from the group consisting of a porcine oocyte, bovine oocyte, ovine oocyte, goat oocyte, horse oocyte, canine oocyte and feline oocyte.

In another aspect, provided herein is a parthenogenetic oocyte activated by the methods of the present invention. In still another aspect, provided herein is a nuclear transfer oocyte activated by the methods of the present invention.

In yet another aspect, the present invention provides a viable livestock or domestic mammalian animal produced from an unfertilized livestock or domestic mammalian oocyte activated by the methods of the invention, wherein the animal comprises the genomic DNA from a donor cell other than the oocyte and the mitochondrial DNA from the oocyte. In certain embodiments, the animal comprises epigenetic features different from the epigenetic features of the donor cell. In particular embodiments, the epigenetic features different from the epigenetic features of the donor cell are DNA methylation sites or histone modifications. In further embodiments, the animal is selected from the group consisting of a porcine animal, bovine animal, ovine animal, goat, horse, dog and cat.

In a further aspect, the present invention provides a method of activating an unfertilized mammalian oocyte comprising increasing intracellular $Ca^{2+}$ concentration of the oocyte by contacting the oocyte with a medium comprising a calcium concentration of approximately 0.1 mM and decreasing intracellular $Zn^{2+}$ concentration of the oocyte by contacting the oocyte with a $Zn^{2+}$ binding moiety at a concentration of approximately 200 µM for a period of time comprising approximately 30 minutes.

In still a further aspect, the present invention provides a method of activating an unfertilized mammalian oocyte comprising increasing intracellular $Ca^{2+}$ concentration of the oocyte by contacting the oocyte with a medium comprising a calcium concentration of approximately 1.0 mM and decreasing intracellular $Zn^{2+}$ concentration of the oocyte by contacting the oocyte with a $Zn^{2+}$ binding moiety at a concentration of approximately 5 µM for a period of time comprising approximately 30 minutes.

In yet a further aspect, the present invention provides a method of activating an unfertilized mammalian oocyte comprising increasing intracellular $Ca^{2+}$ concentration of the oocyte by contacting the oocyte with a medium comprising a calcium concentration of approximately 1.0 mM and decreasing intracellular $Zn^{2+}$ concentration of the oocyte by contacting the oocyte with a $Zn^{2+}$ binding moiety at a concentration of approximately 10 µM for a period of time comprising approximately 30 minutes.

In an additional aspect, the invention provides a method for activating an unfertilized mammalian oocyte, comprising the steps of (a) increasing $Ca^{2+}$ concentration of said oocyte, and (b) subsequently decreasing $Zn^{2+}$ concentration of said oocyte by treatment of $Zn^{2+}$ removing agent. In one embodiment, the $Zn^{2+}$ removing agent is N,N,N',N'-tetrakis(2-pyridylmethyl)ethane-1,2-diamine (TPEN). In another embodiment, the unfertilized mammalian oocyte is a porcine somatic cell nuclear transfer embryo. In yet another embodiment, the TPEN concentration ranges between 0.1 µM to 100 µM. In still another embodiment, the TPEN concentration is 5 µM to 10 µM.

In another aspect, the invention provides a method for activating an unfertilized mammalian oocyte, comprising the steps of (a) providing a minor $Ca^{2+}$ concentration increase of said oocyte, and (b) subsequently decreasing $Zn^{2+}$ concentration of said oocyte by treatment of $Zn^{2+}$ removing agent. In one embodiment, the $Zn^{2+}$ removing agent is N,N,N',N'-tetrakis(2-pyridylmethyl)ethane-1,2-diamine (TPEN). In another embodiment, the unfertilized mammalian oocyte is a porcine somatic cell nuclear transfer embryo. In yet another embodiment, the TPEN concentration is higher than 10 µM. In still another embodiment, the TPEN concentration is 200 µM.

BRIEF DESCRIPTION OF THE DRAWINGS

For a more complete understanding of the features and advantages of the present invention, reference is now made to the detailed description of the invention along with the accompanying figures.

DETAILED DESCRIPTION OF THE INVENTION

Figure 1A:
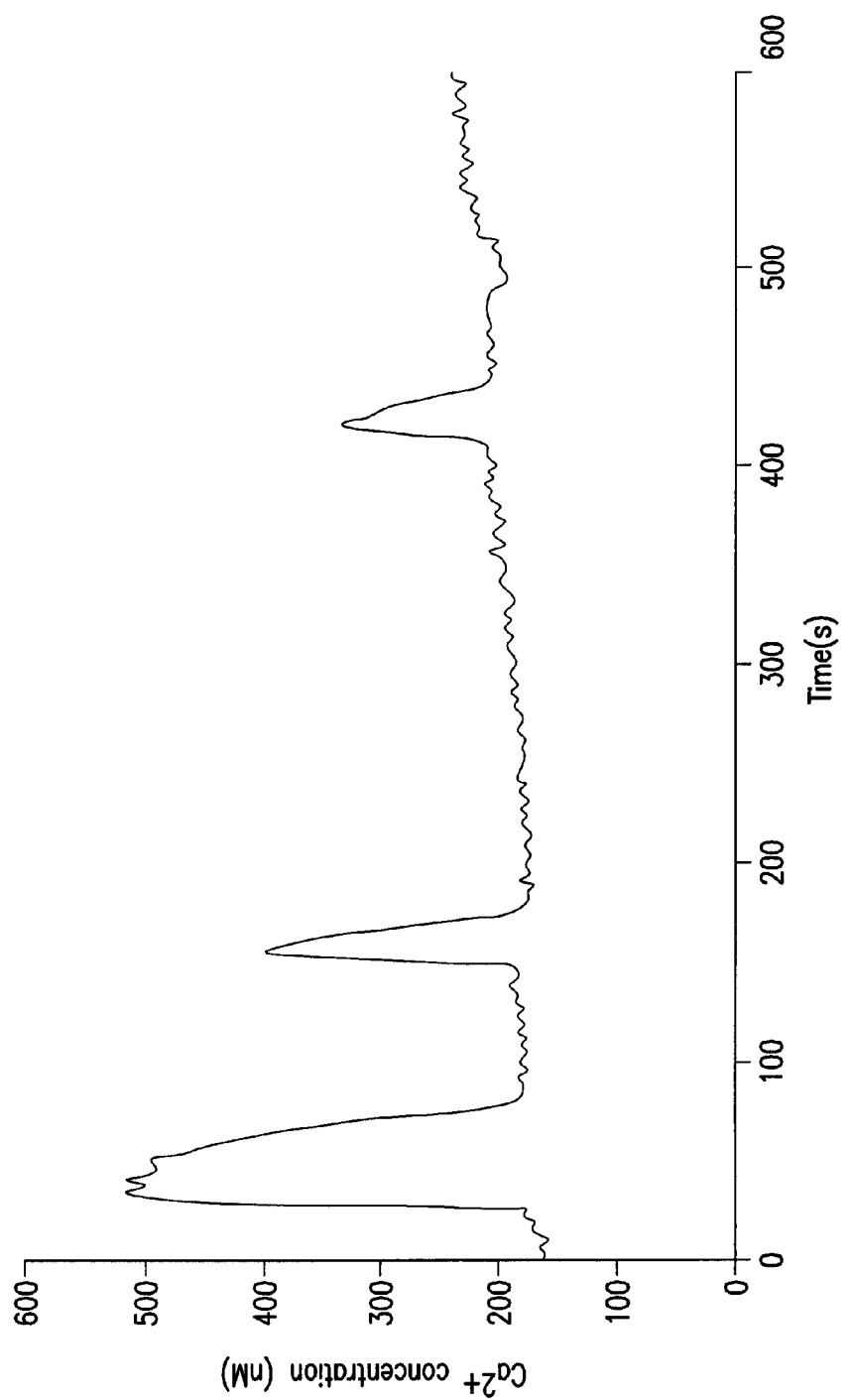
FIG. 1A—Graphical representation demonstrating that N,N,N',N'-tetrakis(2-pyridylmethyl)ethane-1,2-diamine (TPEN) does not induce a $Ca^{2+}$ increase in Metaphase II (MII) oocytes. The graph demonstrates the $Ca^{2+}$ increase after treating MII stage oocytes with thimerosal, an oocyte activating compound.

The present invention provides novel methods for improving the efficiency of artificial oocyte activation of unfertilized mammalian oocytes. In particular, the invention provides methods for oocyte activation through reduction of intracellular $Zn^{2+}$. The methods of oocyte activation of the present invention by reduction of intracellular $Zn^{2+}$ in the unfertilized oocyte may be either independent or dependent of conventional oocyte activation methods. For instance, in one embodiment, the reduction of intracellular $Zn^{2+}$ is sufficient to activate an unfertilized oocyte without being coupled with a prior increase in intracellular $Ca^{2+}$. In another embodiment, the reduction of intracellular $Zn^{2+}$ is preceded by a $Ca^{2+}$ increase in the unfertilized oocyte.

In certain embodiments the $Ca^{2+}$ increase in the unfertilized oocyte may be a minor increase, for instance less than the amount that is sufficient to activate an unfertilized oocyte alone. In another embodiment, the $Ca^{2+}$ increase in the unfertilized oocyte may be an amount equal to or greater than the amount that is sufficient to activate an unfertilized oocyte alone.

Methods for artificial oocyte activation by increasing $Ca^{2+}$ release in the oocyte have been studied with limited success, especially in parthenogenetic and somatic cell nuclear transfer (SCNT) porcine embryo development. Conventional methods to increase intracellular $Ca^{2+}$, including electroporation or thimerosal treatment followed by treatment with dithiothreitol (THI/DTT), are commonly employed in activating SCNT embryos, however, the efficiency and subsequent development is relatively low. The present invention thus provides methods to increase the developmental potential of artificially activated oocytes and increase the efficiency of oocyte activation and subsequent development during SCNT through a treatment with a $Zn^{2+}$ binding moiety and, in certain embodiments, combined with a $Ca^{2+}$ stimulus. The present invention thus overcomes the difficulties in the art regarding artificial oocyte activation by conventional intracellular oocyte $Ca^{2+}$ increase through the use of $Zn^{2+}$ binding moieties, such as $Zn^{2+}$ chelators, for the removal of $Zn^{2+}$.

In nature, penetration of the sperm head into the cytoplasm of the oocyte causes repetitive calcium increases referred as $Ca^{2+}$ oscillations. These oscillations result from the release of phospholipase C (PLC)-zeta from the sperm head. The $Ca^{2+}$ oscillations activate $Ca^{2+}$/calmodulin-dependent protein kinase II (CaMKII) and the CaMKII phosphorylates early mitotic inhibitor 2 (EMI2, also known as FBXO43) thus relieving anaphase-promoting complex/cyclosome (APC/C) from FBXO43-mediated inhibition. These events lead to the degradation of cyclin B, a subunit of M-phase promoting factor (MPF).

Most conventional artificial activation methods induce an intracellular $Ca^{2+}$ increase to mimic this $Ca^{2+}$ signaling. However, because it is technically easier, most artificial activation methods produce a single $Ca^{2+}$ increase, which is suboptimal for activating oocytes, as compared to the repetitive $Ca^{2+}$ increases observed after sperm-induced oocyte activation.

$Zn^{2+}$ is a key component which can maintain oocytes arrested at the metaphase II (MIT) stage and is necessary for activating MPF, as $Zn^{2+}$ regulates the activity of the cyclin-dependent kinase, CDC25. In addition, EMI2 (FBXO43), a zinc-binding protein, is required to maintain high MPF activity during the MII arrest, and the increase in total intracellular $Zn^{2+}$ during oocyte maturation directly controls FBXO43 activity. $Zn^{2+}$ is released from oocytes after fertilization indicating that removal of $Zn^{2+}$ is a natural part of oocyte activation. By utilizing a $Zn^{2+}$ specific binding moiety, such as the $Zn^{2+}$ chelator TPEN, the natural process of oocyte activation can be stimulated thus increasing the developmental potential of activated oocytes.

Artificial oocyte activation is an essential process during SCNT. Unfortunately, current artificial activation methods used during SCNT are suboptimal as they cannot completely emulate the sperm-induced natural signaling pathway. Different strategies have been used to increase the efficiency of artificial oocyte activation by lowering the level of MPF during artificial oocyte activation. However, due to potential toxicity, they are not widely used in cloned animal production, such as pig production.

For the methods of the present invention, intracellular $Ca^{2+}$ concentration may be increased by any conventional method known in the art. Such methods are known in the art would be fully appreciated and understood by one of skill in the art. One exemplary conventional artificial oocyte activation method comprises treating an unfertilized (or nuclear transferred) oocyte with an oocyte-modifying agent, such as thimerosal, followed by a reducing agent, such as dithiothreitol (DTT) (U.S. Pat. No. 6,211,429). Additional methods include, without limitation, various chemical, physical or mechanical stimuli. For instance, the use of a medium comprising any calcium salt, such as $CaCl_2$, or a compound that dissociates calcium; calcium ionophores, such as ionomycin or A23187; use of a sodium-deficient or a sodium-free medium; by electric shock in the presence of $Ca^{2+}$; ethanol treatment; or caged chelators which can release calcium inside the cell in response to specific wavelengths or combinations of one or more of these stimuli. Reference is made to U.S. Pat. No. 6,211,429, which is incorporated herein by reference for a general discussion on increasing intracellular calcium in oocytes and the role of such an increase in artificial oocyte activation.

As used to herein "$Zn^{2+}$ binding moieties" or "$Zn^{2+}$ removing agents" refer to any molecule or composition that is capable of binding, removing or sequestering $Zn^{2+}$. For instance, in certain embodiments, $Zn^{2+}$ binding moieties of the present invention may include $Zn^{2+}$ chelators. Such $Zn^{2+}$ chelators include but are not limited to N,N,N',N'-tetrakis(2-pyridylmethyl)ethane-1,2-diamine (TPEN), known to have a high specificity toward $Zn^{2+}$; clioquinol; and diethylenetriaminepentaacetic acid (DTPA). In particular embodiments, the concentration of $Zn^{2+}$ binding moieties for use in the present invention can comprise approximately 0.01 µM to approximately 1 mM. For instance, from approximately 0.1 µM to approximately 500 µM, approximately 1 µM to approximately 250 µM, approximately 10 µM to approximately 100 µM, approximately 200 µM to approximately 500 µM, approximately 200 µM to approximately 250 µM, approximately 100 µM to approximately 500 µM, approximately 100 µM to approximately 250 µM, approximately 100 µM to approximately 200 µM, approximately 100 µM to approximately 150 µM, approximately 50 µM to approximately 500 µM, approximately 50 µM to approximately 250 µM, approximately 50 µM to approximately 200 µM, approximately 50 µM to approximately 150 µM, approximately 50 µM to approximately 100 µM, approximately 10 µM to approximately 500 µM, approximately 10 µM to approximately 250 µM, approximately 10 µM to approximately 200 µM, approximately 10 µM to approximately 150 µM, approximately 10 µM to approximately 50 µM, approximately 10 µM to approximately 20 µM, approximately 5 µM to approximately 200 µM, approximately 5 µM to approximately 150 µM, approximately 5 µM to approximately 100 µM, approximately 5 µM to approximately 50 µM, approximately 5 µM to approximately 20 µM, approximately 5 µM to approximately 10 µM, approximately 1 µM to approximately 500 µM, approximately 1 µM to approximately 100 µM, approximately 1 µM to approximately 50 µM, approximately 1 µM to approximately 20 µM, approximately 1 µM to approximately 10 µM, approximately 1 µM to approximately 5 µM, approximately 0.1 µM to approximately 100 µM, approximately 0.1 µM to approximately 50 µM, approximately 0.1 µM to approximately 20 µM, approximately 0.1 µM to approximately 10 µM, approximately 0.1 µM to approximately 5 µM, approximately 0.1 µM to approximately 1 µM or a range equivalent thereto.

The concentration of the $Zn^{2+}$ binding moieties may therefore comprise in particular embodiments approximately 0.01 µM, approximately 0.05 µM, approximately 0.1 µM, approximately 0.2 µM, approximately 0.5 µM, approximately 0.75 µM, approximately 1 µM, approximately 2 µM, approximately 3 µM, approximately 4 µM, approximately 5 µM, approximately 6 µM, approximately 7 µM, approximately 8 µM, approximately 9 µM, approximately 10 µM, approximately 11 µM, approximately 12 µM, approximately 13 µM, approximately 14 µM, approximately 15 µM, approximately 16 µM, approximately 17 µM, approximately 18 µM, approximately 19 µM, approximately 20 µM, approximately 25 µM, approximately 30 µM, approximately 35 µM, approximately 40 µM, approximately 45 µM, approximately 50 µM, approximately 55 µM, approximately 60 µM, approximately 65 µM, approximately 70 µM, approximately 75 µM, approximately 80 µM, approximately 85 µM, approximately 90 µM, approximately 95 µM, approximately 100 µM, approximately 110 µM, approximately 120 µM, approximately 130 µM, approximately 140 µM, approximately 150 µM, approximately 160 µM, approximately 170 µM, approximately 180 µM, approximately 190 µM, approximately 200 µM, approximately 210 µM, approximately 220 µM, approximately 230 µM, approximately 240 µM, approximately 250 µM, approximately 300 µM, approximately 350 µM, approximately 400 µM, approximately 450 µM, approximately 500 µM, approximately 550 µM, approximately 600 µM, approximately 650 µM, approximately 700 µM, approximately 750 µM, approximately 800 µM, approximately 850 µM, approximately 900 µM, approximately 950 µM, approximately 1000 µM or an amount equivalent thereto.

The period of time the oocytes are in contact with the $Zn^{2+}$ binding moieties should be a period effective to result in activation thereof either when preceded by an increase in intracellular calcium levels or in the absence of intracellular calcium level increase. Such time periods can be within the range of from approximately 1 minute to approximately 12 hours. For instance, from approximately 1 minute to approximately 5 hours, approximately 1 minute to approximately 2 hours, approximately 1 minute to approximately 1.5 hours, approximately 1 minute to approximately 1 hour, approximately 1 minute to approximately 45 minutes, approximately 1 minute to approximately 30 minutes, approximately 1 minute to approximately 20 minutes, approximately 1 minute to approximately 15 minutes, approximately 1 minute to approximately 10 minutes, approximately 1 minute to approximately 5 minutes, approximately 5 minutes to approximately 12 hours, approximately 5 minutes to approximately 5 hours, approximately 5 minutes to approximately 2 hours, approximately 5 minutes to approximately 1.5 hours, approximately 5 minutes to approximately 1 hour, approximately 5 minutes to approximately 45 minutes, approximately 5 minutes to approximately 30 minutes, approximately 5 minutes to approximately 20 minutes, approximately 5 minutes to approximately 15 minutes, approximately 5 minutes to approximately 10 minutes, approximately 10 minutes to approximately 2.5 hours, approximately 10 minutes to approximately 2 hours, approximately 10 minutes to approximately 1.5 hours, approximately 10 minutes to approximately 1 hour, approximately 10 minutes to approximately 45 minutes, approximately 10 minutes to approximately 30 minutes, approximately 10 minutes to approximately 20 minutes, approximately 10 minutes to approximately 15 minutes, approximately 30 minutes to approximately 2.5 hours, approximately 30 minutes to approximately 2 hours, approximately 30 minutes to approximately 1.5 hours, approximately 30 minutes to approximately 1 hour, approximately 45 minutes to approximately 2.5 hours, approximately 45 minutes to approximately 2 hours, approximately 45 minutes to approximately 1.5 hours, approximately 45 minutes to approximately 1 hour, approximately 1 hour to approximately 2.5 hours, approximately 1 hour to approximately 2 hours, approximately 1 hour to approximately 1.5 hours, approximately 1.5 hours to approximately 2.5 hours, approximately 1.5 hours to approximately 2 hours, approximately 2 hours to approximately 2.5 hours or a range equivalent thereto.

The period of time the oocytes are in contact with the $Zn^{2+}$ binding moieties may therefore comprise, approximately 1 minute, approximately 2 minutes, approximately 3 minutes, approximately 4 minutes, approximately 5 minutes, approximately 6 minutes, approximately 7 minutes, approximately 8 minutes, approximately 9 minutes, approximately 10 minutes, approximately 11 minutes, approximately 12 minutes, approximately 13 minutes, approximately 14 minutes, approximately 15 minutes, approximately 16 minutes, approximately 17 minutes, approximately 18 minutes, approximately 19 minutes, approximately 20 minutes, approximately 25 minutes, approximately 30 minutes, approximately 35 minutes, approximately 40 minutes, approximately 45 minutes, approximately 50 minutes, approximately 55 minutes, approximately 1 hour, approximately 1.25 hours, approximately 1.5 hours, approximately 1.75 hours, approximately 2 hours, approximately 2.25 hours, approximately 2.5 hours, approximately 2.75 hours, approximately 3 hours, approximately 3.5 hours, approximately 4 hours, approximately 4.5 hours, approximately 5 hours, approximately 5.5 hours, approximately 6 hours, approximately 6.5 hours, approximately 7 hours, approximately 7.5 hours, approximately 8 hours, approximately 8.5 hours, approximately 9 hours, approximately 9.5 hours, approximately 10 hours, approximately 10.5 hours, approximately 11 hours, approximately 11.5 hours, approximately 12 hours, or a time equivalent thereto.

For those embodiments of the invention comprising decreasing the intracellular concentration of $Zn^{2+}$ of the unfertilized oocytes preceded by an increase in intracellular $Ca^{2+}$ of the unfertilized oocyte, the step of contacting the oocyte with a $Zn^{2+}$ binding moieties after increasing the intracellular level of $Ca^{2+}$ in the oocyte may occur substantially immediately after the step of increasing the intracellular level of $Ca^{2+}$ or may occur after a period of time comprising from about 5 seconds to about 10 minutes or a range equivalent thereto. The $Zn^{2+}$ binding moiety may be added to the media in which the increase in intracellular $Ca^{2+}$ occurred or the oocyte may be washed or transferred into new media after the increase in intracellular $Ca^{2+}$. In some embodiments, oocytes may be washed to remove the presence of the $Zn^{2+}$ binding moiety after activation. In further embodiments, activation of oocytes may be determined microscopically, by observing pronuclear formation, extrusion of a polar body, division of the oocytes to the 2-cell stage, or subsequent development to the blastocyst stage. Other methods for confirming oocyte activation would be known by one of skill in the art and would be suitable for use with the present method.

The methods described herein are generally applicable to unfertilized oocytes from a wide array of mammalian animals, including, but not limited to, livestock mammals, domestic mammals, model animal mammals, and human or non-human mammals. As used to herein "livestock mammals" refer to any mammalian animal that is useful in an agricultural or livestock setting, such as pig (porcine), cattle (bovine), sheep (ovine), goat, horse and buffalo. "Domestic mammals" refer herein to any mammal that has been domesticated by humans such that they are tame and depend upon man for survival, such as cat (feline), dog (canine), rabbit, guinea pig, and hamster. "Model animal mammals" refer herein to any mammal used for scientific and health related research, such as mice, and rats. In certain embodiments these categories of mammals may overlap, for instance domestic mammals such as dogs may also be classified as a model animal mammal.

In certain embodiments, the present methods of activating unfertilized mammalian oocytes disclosed herein facilitate parthenogenetic development of such eggs so that development thereof can proceed to the 2-cell stage, to at least the blastocyst stage, or anywhere in between, upon culturing in vitro or in vivo. In other embodiments, the present methods of oocyte activation may be employed in the field of mammalian cloning by nuclear transfer. In particular embodiments, the method of the present invention may be used in conjunction with conventional methods of mammalian cloning well known to those skilled in the art. Reference is made to First and Prather (*Differentiation* 48, 1991) and U.S. Pat. Nos. 4,994,384 and 6,211,429, which are incorporated herein by reference for a general discussion on nuclear transfer techniques.

The term "nuclear transfer" as used herein refers to a process of transferring a nucleus of a cell of an adult, fetus, embryo, or cell line (referred to herein as "nuclear donor cell") into an enucleated oocyte (referred to herein as "recipient oocyte"). In certain embodiments, the enucleated oocyte referred to herein may comprise a MII oocyte from which the MII arrested chromosomes have been removed. A MII oocyte is referred to herein as "enucleated" despite comprising chromosomes arrested in metaphase and not comprising a membrane-bound nucleus. Oocytes for use in the present invention may be matured prior to nuclear transfer. Such maturation may be done either in vitro or in vivo using methods known in the art.

The resulting cell obtained by the nuclear transfer is referred to herein as a "nucleus-transferred oocyte," "nuclear transfer oocyte," "somatic cell nuclear transfer oocyte," or "somatic cell nuclear transfer embryo." The term nuclear donor cell may refer to any cell with a nucleus containing two sets of chromosomes (2n).

In certain embodiments, the methods of the present invention may involve the use of donor cells, for example those from a cell line, that have been genetically engineered using methods well known in the art (for instance as disclosed in Ausubel et al., Current Protocols in Molecular Biology, John Wiley & Sons, Inc., 1989, and Sambrook et al., Molecular Cloning: A Laboratory Manual, Second Edition, Cold Spring Harbor Laboratory Press, Cold Spring Harbor, N.Y., 1989) with a gene or other structural coding sequence of interest that may have been genetically modified prior to carrying out nuclear transfer. In this case, the product would be a transgenic animal with a modified characteristic. Alternatively, the donor nucleus may have been genetically modified by using other methods, such as mega-nucleases, that do not necessarily leave a genetic footprint, such as a transgene or selectable marker. Reference is made to Whyte et al. (*Mol. Reprod. Dev.*, 78, 2011), Lee et al. (*PNAS*, 11, 2014), and Whitworth et al. (*Biology of Reproduction*, 91, 2014), for examples of mega-nucleases, such as zinc finger nucleases, TALENs, and CRISPR/Cas9 systems, respectively, the disclosure of which are incorporated herein.

Introduction of a nucleus from a donor cell into an enucleated recipient oocyte to form an oocyte containing the donor nucleus can be performed by fusing together the membrane of a membrane-bound nucleus from the donor cell with the membrane of the enucleated recipient oocyte to form an oocyte containing the nucleus from the donor cell. Alternatively, such introduction can be performed by microinjecting the nucleus from the donor cell into the enucleated recipient oocyte to form an oocyte containing the nucleus from the donor cell. As those of ordinary skill in the art are aware, further alternative means exist for introducing donor nuclear material into a recipient oocyte. For example, and not by way of limitation, one can introduce a donor cell (or nucleus) into the space under the zona pellucida or into the perivitelline space of the enucleated, recipient oocyte, and then subsequently carry out membrane fusion to produce an oocyte containing within its cytoplasm the donor nucleus. All means of introducing donor nuclear material into an enucleated recipient oocyte known to those of ordinary skill in the art are useful in the methods disclosed herein.

In certain embodiments the present invention provides mammalian animals produced though nuclear transfer, also referred to as cloned animals, that result from a nuclear transferred oocyte or nuclear transferred embryo activated by methods disclosed herein. Such animals are distinct from the animals from which the donor nucleus originated, referred to herein as a "donor animal." For instance, in certain embodiments although such cloned animals comprise the same genomic DNA as that of the donor nucleus, cell or animal from which the donor nucleus originated, the cloned animal may comprise distinct characteristics distinguishing it from the donor animal. In particular, embodiments, the cloned animal may comprise mitochondrial DNA or epigenetic traits or characteristics distinct from that of the donor animal. Such distinctions would be well understood and known by those of skill in the art.

Unlike nuclear DNA, mitochondrial DNA of an offspring, including animals produced through nuclear transfer, is inherited from the maternal parent, i.e. from the oocyte. A cloned animal would likely therefore comprise distinct mitochondrial DNA from that of a donor animal. Mitochondrial DNA drives the function of the cell's mitochondria and thus cellular respiration. Distinctions in mitochondrial DNA can therefore result in distinctions in mitochondrial function and cellular respiration.

Additionally, although cloned animals may comprise the same nuclear genomic sequence, the epigenetic markers or features associated with the nuclear genome may in certain embodiments be distinct from those of the donor animal. Although in certain embodiments some epigenetic markers or features may be inherited, referred to as transgenerational epigenetic markers, and thus remain unaltered between donor animal and cloned animal, many epigenetic markers or features are removed during development (referred to in the art as "reprogramming").

Such epigenetic markers or features that may differ between donor and cloned animal may comprise, but are not limited to, DNA methylation, histone modifications, imprinting, gene silencing, and X chromosome inactivation. In particular embodiments of the invention, the result of such epigenetic distinctions between a donor and cloned animal may include distinctions in gene or protein expression, thus may altering the phenotype of resulting animal. One example of such phenotypic distinction between cloned and donor animals can be seen in the original cloned cat, known in the art as "CopyCat." The nuclear donor for CopyCat was a calico cat but due to epigenetic changes between the donor and CopyCat (specifically X inactivation) CopyCat has a coloration distinct from that of the donor cat despite the two cats comprising the same nuclear genome. The genetic and epigenetic differences between cloned and donor animals, including but not limited to those discussed above, are known in the art.

EXAMPLES

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

Example 1

Oocyte Maturation

Oocytes were obtained from either pre-pubertal gilt ovaries from an abattoir (Farmland Foods Inc., Milan, Mo.), or sow-derived oocytes that were purchased from Applied Reproductive Technology (Madison, Wis.). Immature oocytes from gilt ovaries were aspirated from medium size (3-6 mm) follicles by using an 18 gauge hypodermic needle attached to a 10 mL syringe. Oocytes with evenly dark cytoplasm and intact surrounding cumulus cells were then selected for maturation. Around 50 cumulus oocyte complexes were place in a well containing 500 μL of maturation medium, TCM 199 (Invitrogen, Grand Island, N.Y.) with 3.05 mM glucose, 0.91 mM sodium pyruvate, 0.57 mM cysteine, 10 ng/mL epidermal growth factor (EGF), 0.5 mg/mL luteinizing hormone (LH), 0.5 mg/mL follicle stimulating hormone (FSH), 10 ng/mL gentamicin (APP Pharm, Schaumburg, Ill.), and 0.1% polyvinyl alcohol (PVA) for 42-44 hr at 38.5° C., 5% $CO_2$, in humidified air. The oocytes from sows were shipped overnight in maturation medium (TCM199 with 2.9 mM Hepes, 5 mg/mL insulin, 10 ng/mL EGF, 0.5 mg/mL p-FSH, 0.91 mM pyruvate, 0.5 mM cysteine, 10% porcine follicular fluid, 25 ng/mL gentamicin) and transferred into fresh medium at 24 hr. At the end of the maturation, the surrounding cumulus cells were removed from the oocytes by vortexing for 3 min in the presence of 0.1% hyaluronidase. Oocytes with a visible polar body were selected in manipulation medium (TCM 199 with 0.6 mM $NaHCO_3$, 2.9 mM Hepes, 30 mM NaCl, 10 ng/mL gentamicin, and 3 mg/mL bovine serum albumin [BSA]; and osmolarity of 305) and then used for the experiments.

Example 2

Various Oocyte Activation Methods

Different oocyte activation methods were used for the experiments. As conventional activation methods, either electrical or chemical activation was used. For electrical activation, mature oocytes were activated in activation medium (0.3 M mannitol, 1.0 mM $CaCl_2$, 0.1 mM $MgCl_2$, and 0.5 mM Hepes) by two direct-current (DC) pulses (1-sec interval) at 1.2 kV/cm for 30 μsec (using BTX Electro Cell Manipulator, Harvard Apparatus, Holliston, Mass.). For chemical activation, mature oocytes were incubated in Hepes-buffered Tyrode's lactate (TL-Hepes) media in the presence of 200 mM thimerosal for 10 min in the dark followed by 8 mM dithiothreitol for 30 min. For TPEN mediated activation, mature oocytes were incubated in TL-Hepes media with various concentrations of TPEN for different durations.

Activated oocytes were washed three times in PZM3 then incubated at 38.5° C., 5% $CO_2$ until the embryos were examined on either day 2, 6 or 7. At the end of the culture, where applicable, the frequency of cleaved embryos and blastocysts, and total cell number in the blastocysts were recorded. Hoechst 33342 (1.2 mg/mL) was used to stain nuclei and the embryos were then evaluated by epi-fluorescence microscopy.

Example 3

Intracellular Calcium Measurement

The zonae pellucidae were removed after maturation and zona-free oocytes were loaded with the $Ca^{2+}$ indicator dye, fura-2. For this purpose, they were incubated in the presence of 2 mM of the acetoxymethyl ester form of the dye and 0.02% pluronic F-127 for 40-50 min (both from Invitrogen). The dye loaded oocytes were transferred into a chamber with a cover-glass bottom and the chamber was then placed on the heated stage of an inverted microscope. Changes in the intracellular free $Ca^{2+}$ concentration were recorded using InCytIm2, a dual-wavelength fluorescence imaging system (Intracellular Imaging, Inc.; Cincinnati, Ohio). During measurements the emitted fluorescence was detected at 510 nm after exciting the dye alternately at 340 and 380 nm. The ratio of the two emitted fluorescence intensities was calculated and the data are presented as fluorescence ratio values. Ratios of 1.0 and 5.0 correspond to about 100 and 1,200 nM $Ca^{2+}$, respectively. In each treatment group the measurements were repeated at least 5 times using different oocytes.

Example 4

Parthenogenetic Activation of Porcine Oocytes by TPEN

Metaphase II porcine oocytes were incubated in vitro with TPEN to determine if the concentration/duration of 100 μM of TPEN for 45 min, as described in the mouse study by Suzuki, et al. (*Development* 137, 2659-2669, 2010) had any effect on pig oocytes. The protocol described by Suzuki, et al. could activate pig oocytes, however, the development was inferior to conventional artificial activation methods. Frequency of forming blastocysts on day 7 was comparable to the conventional oocyte activation method (13% vs. 15%, respectively) but the rate of blastocyst formation was slower. No blastocyst formation was observed on day 5 with the TPEN treatment whereas 10% of activated embryos reached blastocysts in the control group. In addition, no expanded blastocysts were derived from the TPEN activation group on day 7, indicating lower developmental competency of the embryos derived from the TPEN activation method.

A wide range of TPEN concentrations/durations was tested to identify an optimum concentration of TPEN that can activate pig oocytes; 100 μM, 200 μM, and 250 μM and 30 min-2.5 hours of duration were tested (Table 1). Optimum embryo development was achieved by using 200 μM TPEN for 30 min. Although the frequency of blastocyst formation was not statistically superior to a conventional activation method, a numerical increase in blastocyst formation was observed. A lower total number of nuclei in blastocysts was observed in the embryos derived from the optimal TPEN activation group (200 μM, 30 min), compared to the control (27.2±1.92 vs. 32.6±3.12, respectively, P<0.01). When oocytes were incubated in 250 μM TPEN over 2.5 hours, a toxic effect of TPEN was observed. The 250 μM TPEN treatment over 2.5 hours blocked embryo development as there was no blastocyst formation. An optimum concentration of TPEN which successfully induced development of activated oocytes was identified, but the total number of nuclei in these embryos was lower compared to the conventional activation method.

TABLE 1

Porcine oocytes activated with TPEN alone.

| Treatment | Total number of oocytes | % blastocysts |
|---|---|---|
| Electroporation | 98 | 11.2% |
| 100 μM, 2 hr | 65 | 12.0% |
| 200 μM, 30 min | 25 | 23.0% |
| 200 μM, 1 hr | 79 | 20.0% |
| 250 μM, 2 hr | 30 | 10.0% |
| 250 μM, 2.5 hr | 25 | 0% |

Example 5

Treatment of Activated Oocytes with TPEN

Treatment of activated oocytes with TPEN was investigated for the potential to increase the efficiency of oocyte activation. When chemically activated oocytes were incubated with TPEN (100 μM, 45 min), no blastocyst formation was observed suggesting the combination of the two methods is toxic to embryos. It was hypothesized that the detrimental effect was due to excess stimuli from $Ca^{2+}$ signaling and TPEN. Therefore, lower concentrations of TPEN were introduced after activating oocytes with a conventional method. Incubating activated oocytes with a lower concentration of TPEN increased developmental potential of parthenogenetic embryos. Interestingly, when activated oocytes were incubated with a low concentration of TPEN (5-10 μM) the TPEN treated group surprisingly showed higher developmental potential compared to the control group. Specifically, the average percent blastocyst formation of TPEN treated oocytes (5 μM for 30 min) was 27.2±1.7% but only 10.6±2.5% developed to blastocyst in the control group (Table 2). Moreover, the average number of nuclei in blastocysts was higher in TPEN treated oocytes compared to the control group which was activated by thimerosal/DTT approach (Table 2).

TABLE 2

Incubation of TPEN can increase development potential of activated oocytes. Different letters indicate statistical difference ($p < 0.05$).

| Treatment | Total number of embryos | % cleaved | % Blastocysts | Total cell number in blastocysts |
|---|---|---|---|---|
| THI/DTT | 113 | 59.3$^a$ | 10.6$^a$ | 28.2 ± 2.1$^a$ |
| THI/DTT + 5 μM TPEN, 30 min | 114 | 74.6$^b$ | 27.2$^b$ | 33.1 ± 2.6$^b$ |
| THI/DTT + 10 μM TPEN, 10 min | 83 | 81.9$^b$ | 21.7$^b$ | 31.2 ± 2.6$^b$ |

Next, the optimal concentration and duration of TPEN (5 μM, 30 min) was used to artificially activate reconstructed SCNT embryos. There was an increase in frequency of blastocyst formation when activated SCNT embryos were treated with TPEN (7.9% vs. 18.6%, respectively) (Table 3). This increase in development was comparable to the effect of Scriptaid, a histone deacetylase (HDAC) inhibitor, known to increase developmental potential of SCNT embryos. Thus lower concentrations of TPEN (5-10 μM) can enhance embryo development when introduced after conventional oocyte activation.

TABLE 3

In vitro development of SCNT embryos treated with Scriptaid or TPEN alone. Different letters indicate statistical difference ($p < 0.05$).

| Treatment | Number of embryos | % Blastocysts |
|---|---|---|
| SCNT (control) | 76 | 7.9%$^a$ |
| SCNT + Scriptaid | 194 | 22.7%$^b$ |
| SCNT + 5 μM TPEN, 30 min | 102 | 18.6%$^b$ |

Example 6

TPEN can Serve as the Main Activating Reagent

It was hypothesized that a proper combination of $Ca^{2+}$ signal and TPEN can increase the developmental potential of activated oocytes. The ability of TPEN as the main activating reagent was therefore tested. First, oocytes received an intracellular $Ca^{2+}$ increase through electroporation, although the concentration of $Ca^{2+}$ (0.1 mM) in the electroporation media was not sufficient to induce oocyte activation. Then the oocytes were incubated with various concentrations (1 μM, 5 μM, 10 μM, 100 μM and 200 μM) and durations (10 minutes, 20 minutes, 30 minutes, 1 hour, 2 hours, and overnight) of TPEN. The combination of a smaller $Ca^{2+}$ increase and lower concentration of TPEN (10 μM) resulted in 0 day 6 blastocysts. Surprisingly, oocytes activated by a smaller $Ca^{2+}$ increase followed by TPEN incubation at higher concentration (100 μM or above) could successfully activate oocytes and some combinations resulted in a superior in vitro development compared to the oocytes activated by a conventional method (Table 4). Additionally, oocytes incubated in 1 μM TPEN overnight presented an increased number of blastocysts at day 6 and 7, although the observed cell numbers in day 7 blastocysts were decreased (24.80±7.84) as compared to oocytes incubated in 10 μM TPEN for 1 hour (30.17±5.97), 10 μM TPEN for 2 hours (29.63±10.47) or 100 μM TPEN for 20 minutes (50.75±17.94). Optimal oocyte activation was observed when oocytes were activated by a smaller $Ca^{2+}$ signal followed by incubating in 200 μM TPEN for 30 min.

TABLE 4

Effect of TPEN as a main oocyte activating reagent. Different letters indicate statistical difference ($p < 0.05$).

| Treatment | Number of embryos | Day 6 Blastocysts (%) | Day 7 Blastocysts (%) |
|---|---|---|---|
| Control - electroporation | 80 | 13.75$^a$ | 17.5$^a$ |
| 10 μM, 30 min | 40 | 0$^b$ | 5$^b$ |
| 10 μM, 1 hour | 40 | 15$^a$ | 22.5$^a$ |
| 10 μM, 2 hours | 40 | 15$^a$ | 25$^a$ |
| 100 μM, 10 min | 40 | 15$^a$ | 15$^a$ |
| 100 μM, 20 min | 40 | 25$^a$ | 30$^a$ |
| 200 μM, 30 min | 81 | 37.04$^c$ | 41.98$^c$ |
| 200 μM, 1 hour | 80 | 18.75$^a$ | 27.5$^a$ |

Additionally, the effect of the TPEN activation method alone on the development of SCNT embryos was tested. For this assay, SCNT embryos were activated using either the conventional thimerosal/DTT method or TPEN (TPEN as a major activating reagent). Although no statistical difference was observed, likely due to the small number of observations, a numerical increase was observed for embryos activated using TPEN as the major activating reagent as compared to those activated using the conventional thimerosal/DTT method during SCNT procedure (Table 5).

TABLE 5

Effect of TPEN activation method on the development of SCNT embryos.

| Activation method | Day 6 blastocyst formation | Day 7 blastocyst formation |
|---|---|---|
| THI/DTT | 23.3% (7/30) | 26.7% (8/30) |
| TPEN (200 μM, 30 min) | 25.8% (8/31) | 35.5% (11/31) |

Example 7

No $Ca^{2+}$ Increase is Observed in Pig Oocytes after Exposure to TPEN

Figure 1B:
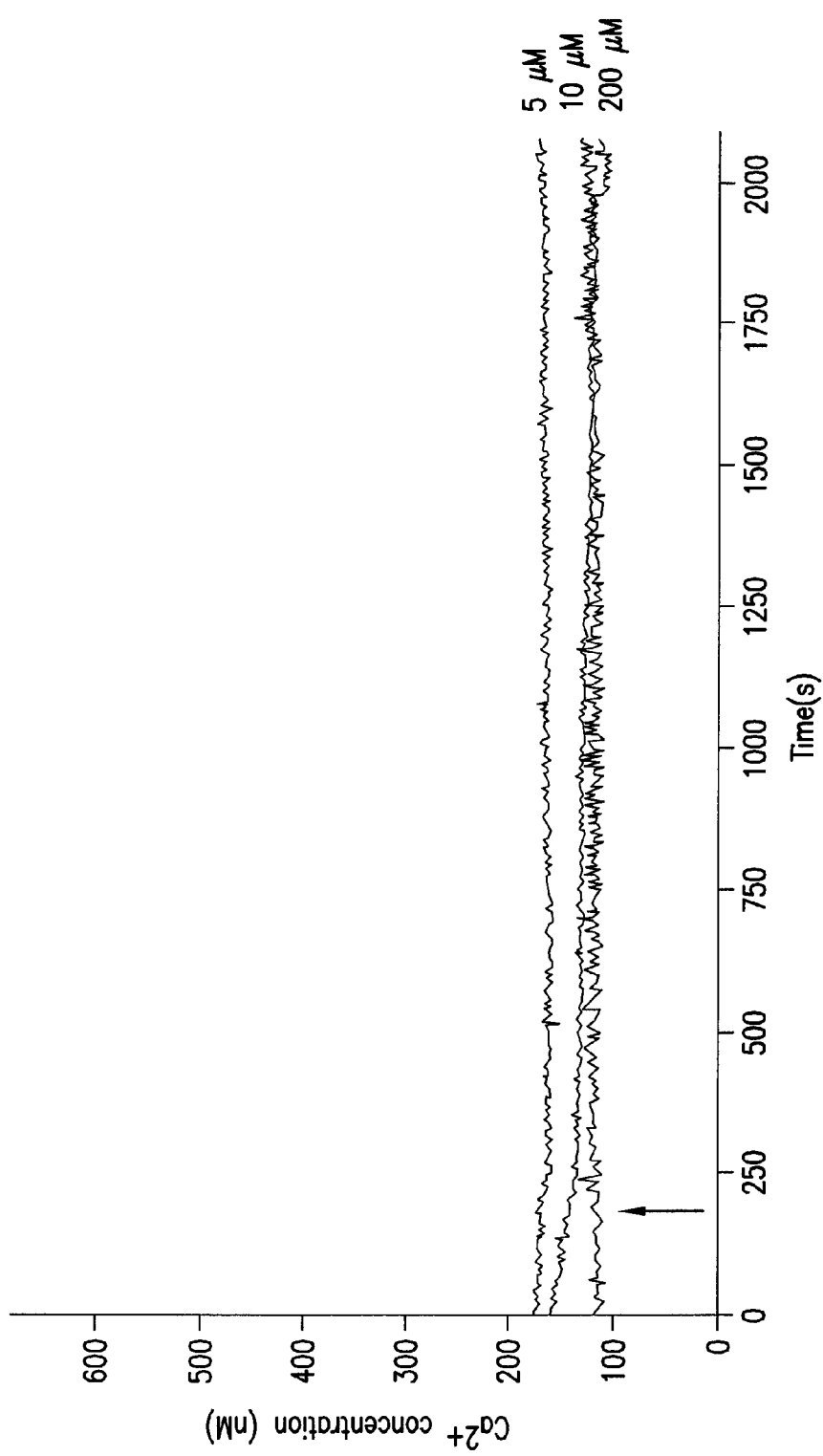
FIG. 1B—Graphical representation demonstrating that TPEN does not induce a $Ca^{2+}$ increase in MII oocytes. The graph demonstrates the lack of $Ca^{2+}$ increase from TPEN. No $Ca^{2+}$ increase was detected when MII stage oocytes were exposed to various concentrations of TPEN. The arrow indicates when the MII oocytes were exposed to TPEN.

To demonstrate that TPEN treatment is stimulating signaling pathways independent of $Ca^{2+}$ signaling, oocytes were exposed to TPEN then the amount of intracellular $Ca^{2+}$ was measured. As expected, no $Ca^{2+}$ increase was detected when oocytes were exposed to a range of TPEN (5, 10, and 200 μM), while oocytes incubated with thimerosal, serving as a positive control, could induce $Ca^{2+}$ increase (FIG. 1).

This indicates that the benefit of TPEN observed during oocyte activation experiments is independent of $Ca^{2+}$ signaling pathway.

Example 8

In Vivo Development Competence of SCNT Embryos Activated by Utilizing TPEN

To address in vivo competency of SCNT embryos activated by utilizing TPEN, a series of embryo transfers were performed. For the study, at day 1, the SCNT-derived embryos were surgically transferred into the ampullary-isthmic junction of a surrogate gilt at 0 or 1 days after observed estrus. At the end of gestation periods, piglets were recovered through C-section.

Six embryo transfers were performed for the study and two surrogates carried their pregnancy to term, each resulting in two healthy piglets (Table 6). One of the term development was from SCNT embryos that were not treated with a HDAC inhibitor, Scriptaid. The resulting full term development indicates that TPEN is compatible with SCNT development to term and suggests that the TPEN technology is not toxic to the SCNT embryos. None of the resulting animals displayed any health related issues at birth as are sometime observed with cloned animals, and they have produced progeny.

TABLE 6

Result of embryo transfer.

| Treatment | Number of embryos transferred | Result |
|---|---|---|
| SCNT + 5 µM TPEN, 30 min + Scriptaid | 207 | 2 normal piglets were delivered |
| SCNT + 5 µM TPEN, 30 min + Scriptaid | 245 | Cycled |
| SCNT + 10 µM TPEN, 10 min + Scriptaid | 180 | Cycled |
| SCNT + 5 µM TPEN, 30 min | 280 | 2 normal piglets were delivered |
| SCNT + 5 µM TPEN, 30 min | 230 | Cycled |
| SCNT + 5 µM TPEN, 30 min | 280 | Cycled |

Example 9

Statistical Analysis

Differences in the frequency of blastocyst formation was determined after analysis of variance (ANOVA) using the PROC MIX procedure of the Statistical Analysis System (SAS Institute, Cary, N.C., USA) or Chi-square test. Percentage data was arcsin transformed prior to the ANOVA analysis. Average total number of nuclei in blastocysts was compared by using the Student's T-test. Differences with $P<0.05$ were considered significant.

What is claimed is:

1. A method of activating an unfertilized porcine oocyte comprising decreasing intracellular $Zn^{2+}$ concentration of the oocyte by contacting the oocyte with a $Zn^{2+}$ binding moiety comprising approximately 200 µM TPEN (N,N,N', N'-tetrakis(2-pyridylmethyl)ethane-1,2-diamine), wherein the contacting results in activating the oocyte.

2. The method of claim 1, wherein the $Zn^{2+}$ binding moiety contacts the oocyte for a period of time comprising between approximately 30 minutes to approximately 2.5 hours.

3. The method of claim 2, wherein the $Zn^{2+}$ binding moiety contacts the oocyte for a period of time comprising approximately 30 minutes.

4. The method of claim 1, wherein the unfertilized porcine oocyte is a nuclear transfer oocyte.

* * * * *